(12) United States Patent
Asada

(10) Patent No.: US 10,098,778 B1
(45) Date of Patent: Oct. 16, 2018

(54) COMPLIANT BODY SUPPORT SYSTEM FOR CROUCHING AND KNEELING WORK

(71) Applicant: Boston Incubator Center, LLC, Waltham, MA (US)

(72) Inventor: Haruhiko Harry Asada, Lincoln, MA (US)

(73) Assignee: Boston Incubator Center, LLC, Lexington, MA (US)

( * ) Notice: Subject to any disclaimer, the term of this patent is extended or adjusted under 35 U.S.C. 154(b) by 0 days.

(21) Appl. No.: 15/615,608

(22) Filed: Jun. 6, 2017

Related U.S. Application Data

(60) Provisional application No. 62/352,550, filed on Jun. 20, 2016.

(51) Int. Cl.
*A61H 1/00* (2006.01)
*A61F 5/02* (2006.01)
*A61H 1/02* (2006.01)

(52) U.S. Cl.
CPC ............ *A61F 5/028* (2013.01); *A61H 1/0229* (2013.01); *A61H 2001/0203* (2013.01); *A61H 2201/1626* (2013.01); *A61H 2201/1671* (2013.01)

(58) Field of Classification Search
CPC .............................. A61F 5/028; A61H 1/0229
USPC ............................ 248/688; 601/5, 33, 34, 35
See application file for complete search history.

(56) References Cited

U.S. PATENT DOCUMENTS

| 7,325,868 B2* | 2/2008 | West | A47C 16/00 297/4 |
|---|---|---|---|
| 2002/0100846 A1* | 8/2002 | Tinsley | A61G 13/12 248/118 |
| 2014/0346316 A1* | 11/2014 | Sitzmann | A01D 46/243 248/688 |
| 2017/0259427 A1* | 9/2017 | Asada | B25J 9/0006 |

* cited by examiner

*Primary Examiner* — Todd M Epps
(74) *Attorney, Agent, or Firm* — Spano Law Group; Joseph S. Spano

(57) ABSTRACT

Methods and systems for passively supporting the upper body of a human user working at or near the ground are described herein. In one aspect, an upper body support system braces the torso of a human user against a surface of the work environment. This frees the hands and arms of the human user that would otherwise be occupied supporting the human torso. This enables a human user to comfortably use both hands to execute a particular work task. The upper body support system performs the support functionality described herein without the use of active devices. The upper body support system includes one or more passive upper body support assemblies each coupled to a harness assembly worn by the human user. Each passive upper body support assembly includes an extensible body support limb that extends toward the surface of the working environment and supports the human user compliantly.

20 Claims, 9 Drawing Sheets

COMPLIANT BODY SUPPORT SYSTEM FOR CROUCHING AND KNEELING WORK

CROSS REFERENCE TO RELATED APPLICATIONS

The present application for patent claims priority under 35 U.S.C. § 119 from U.S. provisional patent application Ser. No. 62/352,550, entitled "Compliant Body Support System for Crouching and Kneeling Work," filed Jun. 20, 2016, the subject matter of which is incorporated herein by reference in its entirety.

TECHNICAL FIELD

The described embodiments relate to systems and methods for supporting the body of a human user at an ergonomically proper posture while performing tasks for a long period of time.

BACKGROUND INFORMATION

Workers often have to interact with objects located on or near the floor of the work environment. To reach these objects, a worker must assume ergonomically challenging positions including kneeling, crouching, leaning, or some combination thereof. Assuming these positions over a long period of time often leads to injuries to the lower back, knees, ankles, feet, etc. In some examples, manufacturing tasks involve interacting with workpieces located at or near the floor (e.g., welding and assembly tasks in the production of aircraft, automobiles, heavy machinery, ships, construction machines, agricultural equipment, etc.). In some other examples, construction tasks involve interacting with workpieces at or near the floor (e.g., installation of floor tiles, assembly of steel rods for concrete reinforcement, etc.). In some other examples, agricultural tasks involve interacting with objects at or near the ground (e.g., planting flowers, bulbs, and saplings, removing weeds, spreading plant food, harvesting fruits and vegetables, etc.).

Many of these tasks require the use of both hands. In one example, a welder must hold both the welding torch and feed material. Such tasks further complicate worker posture. When one arm is not available to support the upper body, the stresses induced on other parts of the body are increased, further enhancing the risk of fatigue, injury, and accidents.

In summary, improvements in the design of systems to enhance occupational safety in work environments that require laborers to interact with objects at or near the floor of the work environment are desired. More specifically, systems to support the upper body effectively; allowing both hands to be free to perform tasks are desired.

SUMMARY

Methods and systems for passively supporting the upper body of a human user working at or near the ground are described herein. In one aspect, an upper body support system braces the torso of a human user against a surface of the work environment. This frees the hands and arms of the human user that would otherwise be occupied supporting the human torso. Thus, a human user is able to comfortably use both hands to execute a particular work task. In another aspect, the upper body support system performs the support functionality described herein without the use of active devices such as actuators.

In a further aspect, each passive upper body support assembly is coupled to the harness assembly by a rotational joint having at least one degree of freedom that is locked to a desired orientation during use. In some embodiments, the locking and unlocking of the rotational joint is controlled by a control element mounted to the harness assembly within reach of the human user.

In another further aspect, each passive upper body support assembly includes an extensible body support limb that extends toward the surface of the working environment and supports the human user compliantly. In this manner the human user can move the upper body freely to change posture without losing support. In some embodiments, the nominal length of the extensible body support limb is adjustable.

In another further aspect, each passive upper body support assembly includes an extensible body support limb coupled to a housing by a rotational joint that allows the extensible body support limb to rotate with respect to the housing in at least one degree of freedom in a compliant manner. In this manner the human user can move the upper body freely to change posture without losing support. In some embodiments, a passive upper body support assembly includes a compliant toroid having an outer perimeter coupled to the housing and an inner perimeter coupled to the extensible body support limb. The compliant toroid is located at a distance from the rotational joint. In some embodiments, the distance is adjustable. In some embodiments, the distance is adjustable based on a movement of a control element mounted to the harness assembly within reach of the human user.

The foregoing is a summary and thus contains, by necessity, simplifications, generalizations, and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for passively supporting the upper body of a human user working at or near the ground are described herein. In one aspect, an upper body support system braces the torso of a human user against a surface of the work environment. This frees the hands and arms of the human user that would otherwise be occupied supporting the human torso. In this manner, a human user is able to comfortably use both hands to execute a particular work task.

In a further aspect, the upper body support system performs the support functionality described herein without the use of active devices such as actuators.

Figure 1:
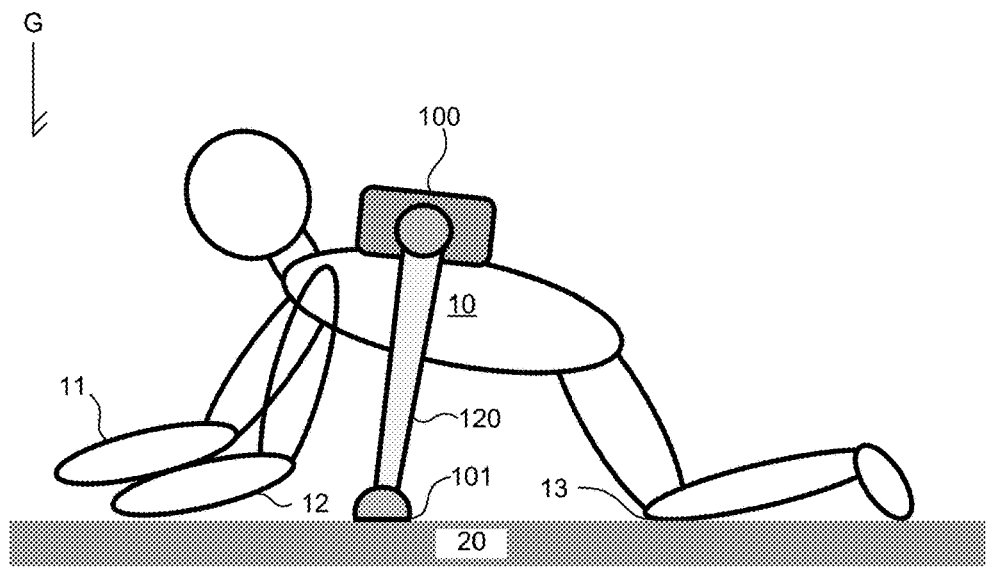
FIG. 1 depicts an upper body support system 100 in one operational scenario.

FIG. 1 depicts an upper body support system 100 in one operational scenario. Upper body support system 100 is attached to the torso 10 of a human user with a harness assembly. Two passive upper body support assemblies 120 are coupled to the harness assembly, one on each side of the body of the human user (i.e., in the direction perpendicular to the drawing sheet). As depicted in FIG. 1, the human user is working on the ground surface 20 oriented perpendicular to the gravity vector, G. The human user is stably supported at the ground surface at contact areas 13 associated with each knee and at contact areas 101 associated with each passive upper body support assembly 120. As depicted in FIG. 1, the upper body of the human user is stably supported by upper body support system 100 without the use of hands 11 and 12. In this manner both hands 11 and 12 are available to perform a task at or near the ground surface 20.

Figure 2:
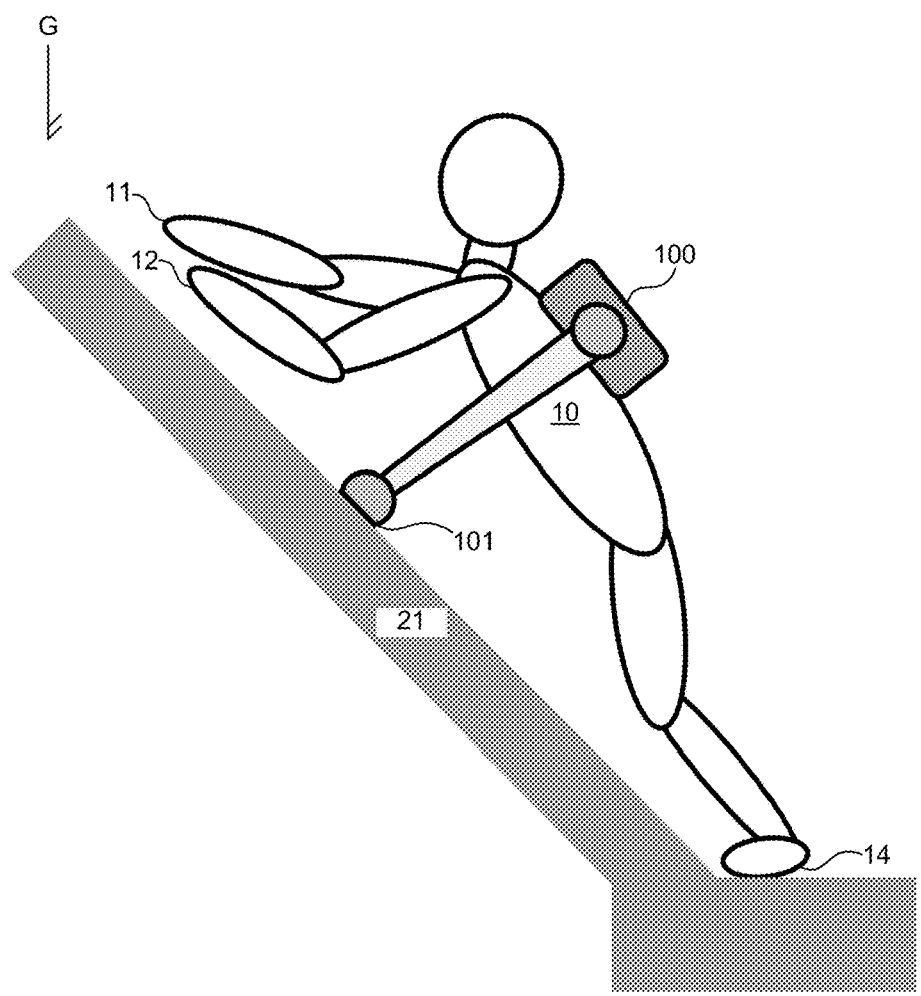
FIG. 2 depicts upper body support system 100 in another operational scenario.

FIG. 2 depicts upper body support system 100 in another operational scenario. Like numbered elements are analogous to those described with reference to FIG. 1. As depicted in FIG. 2, the human user is working on a ground surface 21 oriented at an oblique angle with respect to the gravity vector, G. In some examples, the oblique angle is greater than thirty degrees. In some other examples, the oblique angle is greater than forty five degrees. As depicted in FIG. 2, the human user is stably supported at the ground surface at contact areas 14 associated with each foot of the human user and at contact areas 101 associated with each passive upper body support assembly 120. As depicted in FIG. 2, the upper body of the human user is stably supported by upper body support system 100 without the use of hands 11 and 12. In this manner both hands 11 and 12 are available to perform a task at or near the ground surface 21.

As depicted in FIGS. 1 and 2, two passive upper body support assemblies 120, combined with the lower limbs of the human user provide stable support of the entire body mass. This leaves the arms and hands of the human user freely available to perform the task at hand, such as a task that requires both human hands. In the examples depicted in FIGS. 1 and 2, the upper body support system 100 is located near the center of mass of the human torso, and is configured to support most of the weight associated with the human torso. This reduces the loading on the knees, feet, and back of the human user compared to crouching or kneeling in a conventional manner. As depicted in FIGS. 1 and 2, the knees of the human user are comfortably posed, for example at angles between ninety degrees and one hundred thirty five degrees. The knees do not have to be bent sharply at acute angles to stably support the human body. By distributing the weight of the human body over the passive upper body support assemblies 120, the total amount of load carried by the knees and the severity of the pose required to stably support the human body are significantly reduced.

Although FIGS. 1 and 2 illustrate the use of two passive upper body support assemblies, in general, an upper body support system 100 may employ any number of passive upper body support assemblies. In addition, the upper body support system 100 may be located in any suitable location with respect to the human torso. However, it is preferable to locate the upper body support system 100 in a location that stably supports the human body weight, while minimizing the weight supported by other members of the human body, such as the knees or feet.

Figure 3:
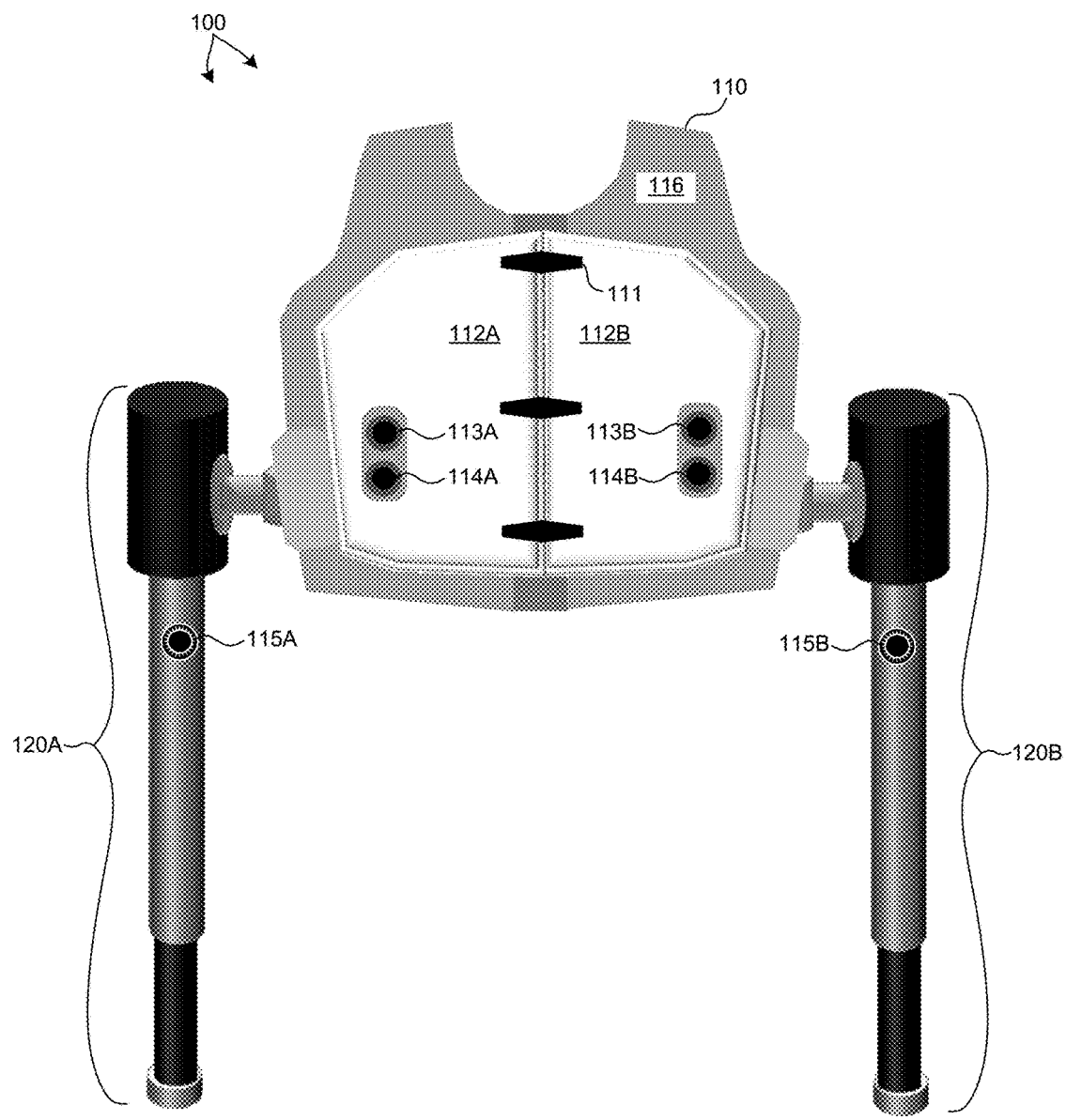
FIG. 3 depicts a front view of upper body support system 100 in one embodiment.

FIG. 3 depicts a front view of upper body support system 100 in one embodiment. Upper body support system 100 includes a harness assembly 110 and two passive upper body support assemblies 120A-B. Harness assembly 110 includes a vest 116 tailored to fit the human user. A human user dons the vest 116 in a conventional manner and cinches the vest onto his/her body using locking mechanisms 111 (e.g., buckles, cinch straps, etc.). Similarly, to remove harness 110, the human user unlocks the vest using locking mechanisms 111 and removes the vest 116 in a conventional manner. In some embodiments, harness assembly 110 includes reinforcing plates 112A-B attached to the fabric of vest 116. Reinforcing plates 112A-B are molded to the body shape of the human user and distribute the load of the upper body over a large area of the human torso. In this manner, stress concentrations on the human body are avoided.

Passive upper body support assemblies 120A-B are each coupled to harness assembly 110. As depicted in FIG. 3, passive upper body support assembly 120A is coupled to the harness assembly 110 on the right side of the human user. Similarly, passive upper body support assembly 120B is coupled to the harness assembly 110 on the left side of the human user. By coupling the passive upper body support assemblies 120A-B on opposite sides of the human user, upper body support system 100 is able to stably support the upper body of the human user.

Figure 4:
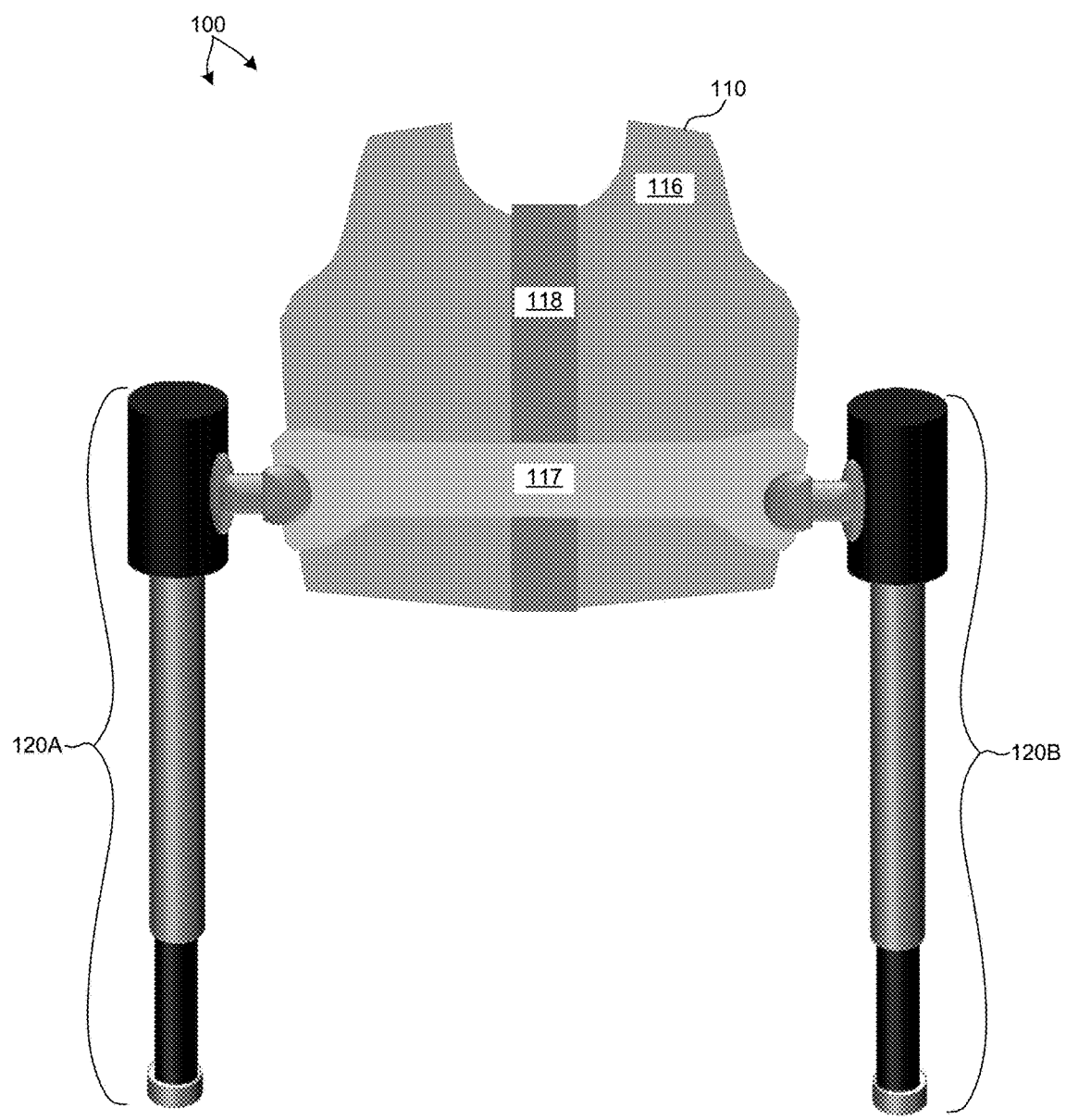
FIG. 4 depicts a back view of upper body support system 100 in one embodiment.

FIG. 4 depicts a back view of upper body support system 100 in one embodiment. As depicted in FIG. 2, harness assembly 110 includes a lateral support member 117 and a longitudinal support member 118 attached to the fabric of vest 116. Lateral support member 117 and longitudinal support member 118 maintain the positioning of the passive upper body support assemblies 120A-B under load distribute the load evenly across the front reinforcing plates 112A-B. Members 117 and 118 are relatively stiff structural members that deform very little under load. This does not result in stress concentrations on the human body because they are not in direct contact with the human body during use.

In some embodiments, the harness assembly 110 is tailored to an individual human user by fabricating one or more components with 3D printing technology. In particular, reinforcing plates 112A-B are shaped to fit the human user precisely to enable a tight fit and large contact area that equalizes the pressure across the entire chest.

In a further aspect, each passive upper body support assembly is coupled to the harness assembly by a rotational joint having at least one degree of freedom that is locked to a desired orientation during use.

Figure 5:
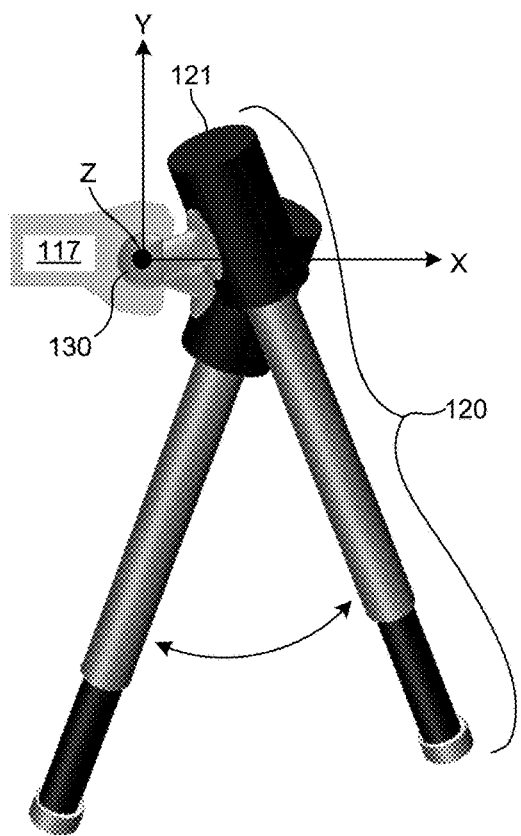
FIG. 5 depicts an illustration of a passive upper body support assembly 120 coupled to lateral support member 117 at housing 121 with a ball and socket joint 130.

FIG. 5 depicts an illustration of a passive upper body support assembly 120 coupled to lateral support member 117 at housing 121 with a ball and socket joint 130. In this embodiment, passive upper body support assembly 120 is free to rotate in three degrees of freedom (e.g., $R_x$, $R_y$, and $R_z$) with respect to lateral support member 117 in an unlocked state. When a desired orientation is realized, the ball and socket joint 130 is locked to fix the orientation of passive upper body support assembly 120 with respect to lateral support member 117 during use.

Figure 6:
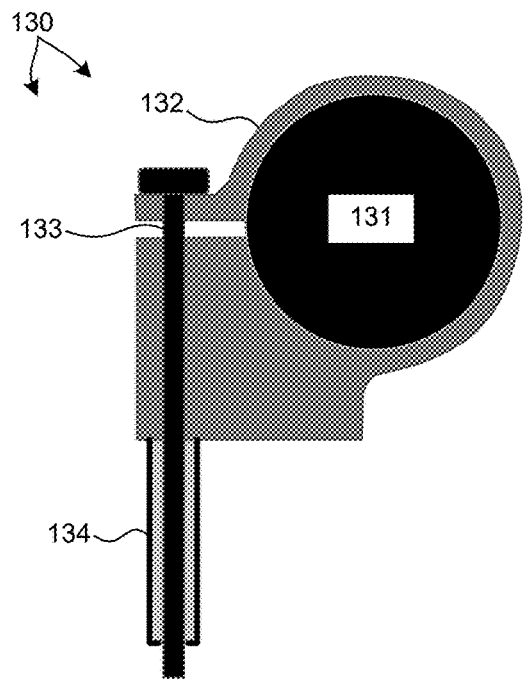
FIG. 6 depicts an illustration of ball and socket joint 130 including a locking mechanism.

FIG. 6 depicts an illustration of ball and socket joint 130 including a locking mechanism. Ball and socket joint 130 includes a ball 131 fixedly coupled to housing 121 and a socket 132 fixedly coupled to lateral support member 117. As depicted in FIG. 6, socket 132 is an elastic member. The size of the socket is adjustable based on the position of cable 133 with respect to cable sheath 134. When cable 133 is placed in tension, socket 132 clamps down on ball 131, locking ball 131 with respect to socket 132. This effectively locks the position and orientation of housing 121 with respect to lateral support member 117. When the tension in cable 133 is released, socket 132 opens up slightly and releases ball 131, allowing housing 121 to be freely oriented with respect to lateral support member 117 with little resistance.

In a further aspect, the tension in cable 133 is controlled by a control element (e.g., ratcheting lever, threaded control knob, etc.) mounted to the harness assembly within reach of the human user. For example, control element 113A controls the tension in cable 133 associated with a ball and socket joint between passive upper body support assembly 120A and harness assembly 110. Similarly, control element 113B controls the tension in cable 133 associated with a ball and socket joint between passive upper body support assembly 120B and harness assembly 110. As depicted in FIG. 3, control elements 113A-B are located on the chest of vest 116 and are easily accessible by a hand of the human user.

Rotational joint 130 is described with reference to FIG. 5 as a ball and socket joint by way of non-limiting example. In general, any suitable rotational joint (e.g., hinge, gimbal, etc.) may be contemplated within the scope of this patent document. Similarly, an elastic socket 132 controlled by a cable 133 and sheath 134 is described with reference to FIG. 6 by way of non-limiting example. In general, any suitable lockable rotational joint and associated mechanism for locking the lockable joint may be contemplated within the scope of this patent document.

In some embodiments, upper body support system 100 rigidly supports the upper body of the human user during operation. However, when body support is rigid, the movement of the human is constrained by the upper body support system. In some working scenarios this may be desirable. However, in other working scenario the constraint may interfere with task performance. Thus, in some embodiments it is advantageous to support the human user in a compliant manner. In this manner, the human user can freely change posture and position while being supported by the upper body support system.

In a further aspect, each passive upper body support assembly 120 includes an extensible body support limb coupled to housing 121. Each extensible body support limb extends toward the surface of the working environment and supports the human user compliantly. In this manner the human user can move the upper body freely to change posture without losing support.

Figure 7A:
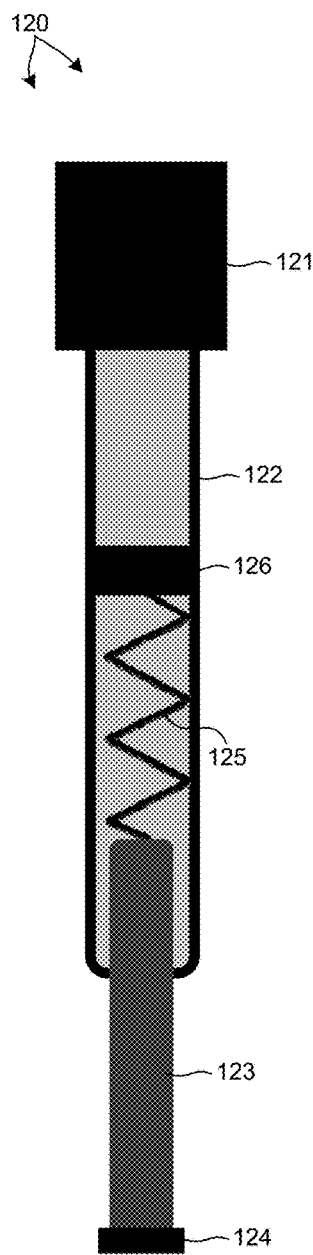
FIGS. 7A-7C depict illustrations of passive upper body support assembly 120 in three different operational scenarios.
Figure 7B:
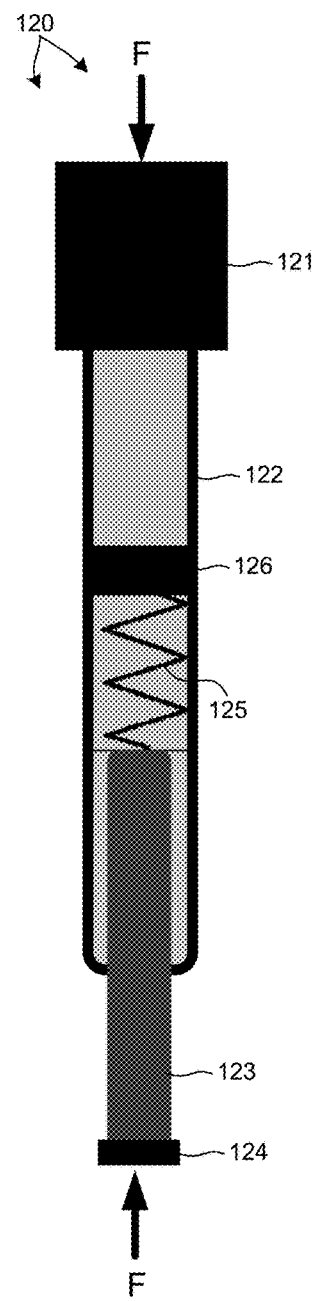
Figure 7C:
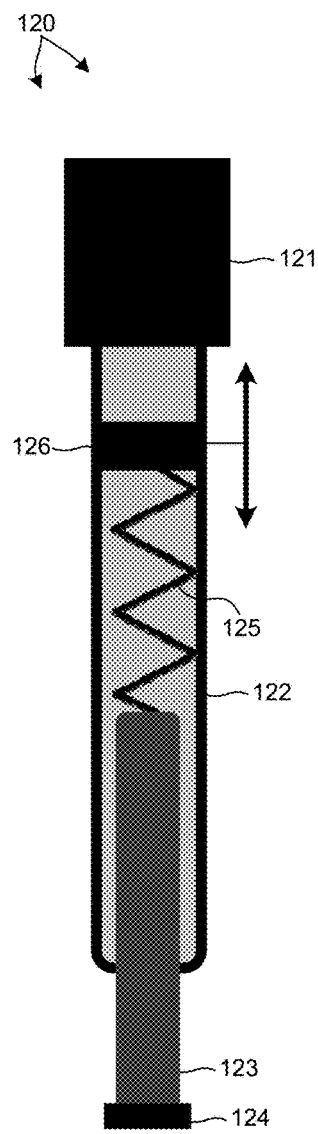

FIGS. 7A-7C depict illustrations of passive upper body support assembly 120 in three different operational scenarios.

As depicted in FIG. 7A, passive upper body support assembly 120 includes housing 121 and an extensible body support limb including a first linear structure 122 coupled to housing 121, a second linear structure 123, and a foot 124 coupled to structure 123. Structure 123 is coupled to structure 122 such that structure 123 moves linearly with respect to structure 122 in one degree of freedom. As depicted in FIG. 7A, structures 122 and 123 form a prismatic joint (e.g., a telescopic mechanism). In this manner, the total length of the extensible body support limb is variable. A spring element 125 is coupled to structure 122 and structure 123. Spring element 125 generates a restoring force in a direction opposite a movement of structure 123 with respect to structure 122 from a nominal position.

FIG. 7B depicts an illustration of passive upper body support assembly 120 under load, F.

In a further aspect, the nominal position (i.e., unloaded position) of structure 123 with respect to the structure 122 is adjustable. In this manner, the unloaded length of the extensible body support limb is adjustable.

FIGS. 7A-C depict a spring adjustment block 126 removably coupled to structure 122. In a locked configuration, spring adjustment block 126 is fixedly coupled to structure 122 and provides a fixed endstop for spring element 125. In an unlocked configuration, the location of spring adjustment block 126 is moveable with respect to structure 122. For example, FIG. 7C depicts spring adjustment block 126 in a different position with respect to structure 122 than FIGS. 7A-B.

In some embodiments, the position of spring adjustment block 126 with respect to structure 122 is adjustable based on a movement of a control element within reach of the human user. For example, as depicted in FIG. 3, control element 115A controls the location of spring adjustment block 126 with respect to structure 122, and hence of the unloaded length of passive upper body support assembly 120A. Similarly, control element 115B controls the location of spring adjustment block 126 with respect to structure 122, and hence the unloaded length of passive upper body support assembly 120B. As depicted in FIG. 3, control elements 115A-B are located on the passive upper body support assemblies 120A-B, respectively, and are easily accessible by a hand of the human user. In one embodiment, control elements 115A-B are spring loaded detents coupled to spring adjustment block 126. When these detents are compressed by a user block 126 is moveable with respect to structure 122. When the detents are released, block 126 is locked in position with respect to structure 122.

Foot structure 124 is the mechanical interface between upper body support system 100 and the surface of the working environment. As depicted in FIG. 4, foot structure 124 is a pad structure (e.g., polymer pad, rubber pad, etc.). However, in general, any suitable structure may be employed. In some embodiments, the foot structure is a wheel that allows the user to move upper body support apparatus 100 in a particular direction along the support surface. In some embodiments, the foot structure is a ball wheel that allows the user to move upper body support structure 100 in any direction along the support surface. When the human user wishes to move in a particular direction, he/she pushes laterally against the ground with his/her knees, feet, or both. This causes the ball wheel to roll in the desired direction without the use of actuators or other active devices. In some embodiments, the foot structure is a gripper mechanism that rigidly couples the upper body support system 100 to the support surface.

Depending on the condition of the floor surface as well as the nature of a given task, different foot structures may be employed. For example, if the floor is flat with no obstacles or steps, wheeled feet can be used for smooth transportation across the floor. If the floor is slippery, a picket-type foot structure may be employed to secure each limb on the floor.

In a further aspect, each passive upper body support assembly 120 includes an extensible body support limb coupled to housing 121 by a compliant rotational joint that allows the extensible body support limb to rotate with respect to the housing in at least one degree of freedom in a compliant manner. In this manner the human user can move the upper body freely to change posture without losing support. In general, the compliant rotational joint may be any suitable compliant rotational joint that allows an extensible body support limb to compliantly rotate with respect to the harness assembly in at least one degree of freedom (e.g., spring loaded hinge, spring loaded ball joint, etc.).

Figure 8:
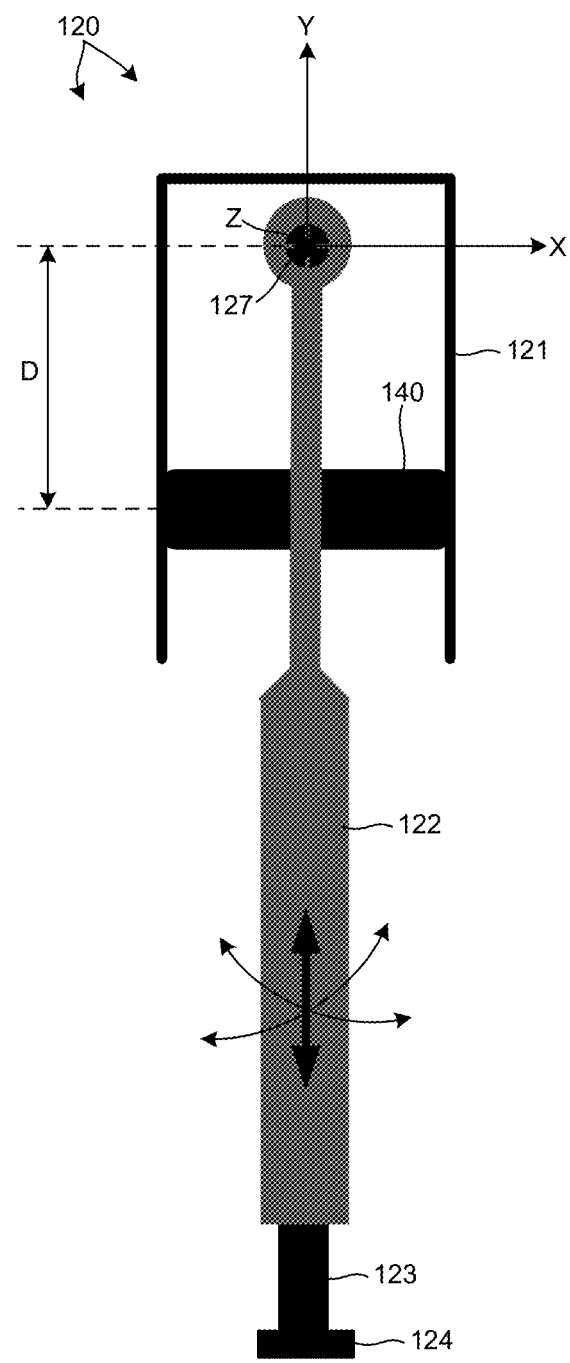
FIG. 8 depicts an illustration of passive upper body support assembly 120 including an extensible body support limb that is rotatable with respect to housing 121.

FIG. 8 depicts an illustration of passive upper body support assembly 120 including an extensible body support limb that is rotatable with respect to housing 121. Passive upper body support assembly 120 includes structures 122 and 123 and foot structure 124 as described with reference to FIGS. 7A-C. In addition, passive upper body support assembly 120 includes a rotational joint 127 that couples the extensible body limb to housing 121.

Rotational joint 127 allows the extensible body limb to rotate with respect to housing 121 in at least one degree of freedom. In one embodiment, rotational joint 127 is a U-joint or a gimbal that allows the extensible body limb to rotate with respect to housing 121 in two degrees of freedom (e.g., $R_x$ and $R_z$).

In a further aspect, passive upper body support assembly 120 includes a compliant toroid 140 having an outer perimeter coupled to the housing and an inner perimeter coupled to the extensible body support limb. As depicted in FIG. 8, compliant toroid 140 is located at a distance, D, from rotational joint 127.

Compliant toroid 140 generates a restoring force in a direction opposite a movement of the extensible body support limb with respect to the housing from a nominal position at the location of compliant toroid 140. As depicted in FIG. 8, the nominal position of the extensible body support limb with respect to housing 121 at compliant toroid 140 is associated with a nominal orientation of the extensible body support limb with respect to housing 121. As the extensible body support limb rotates with respect to housing 121 about rotational joint 127, the extensible body support limb moves with respect to housing 121 at the location of compliant toroid 140. In response, compliant toroid 140 generates a restoring force toward the nominal position.

Figure 9A:
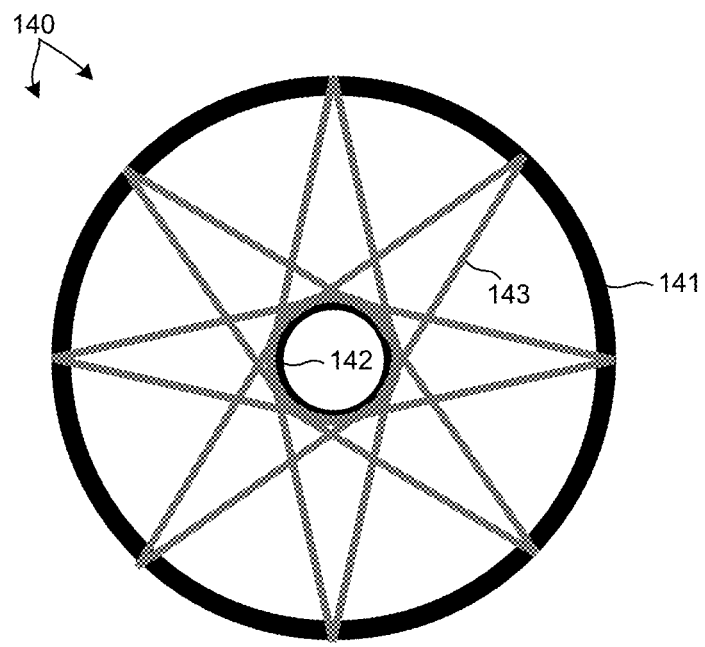
FIG. 9A depicts compliant toroid 140 in a nominal position.
Figure 9B:
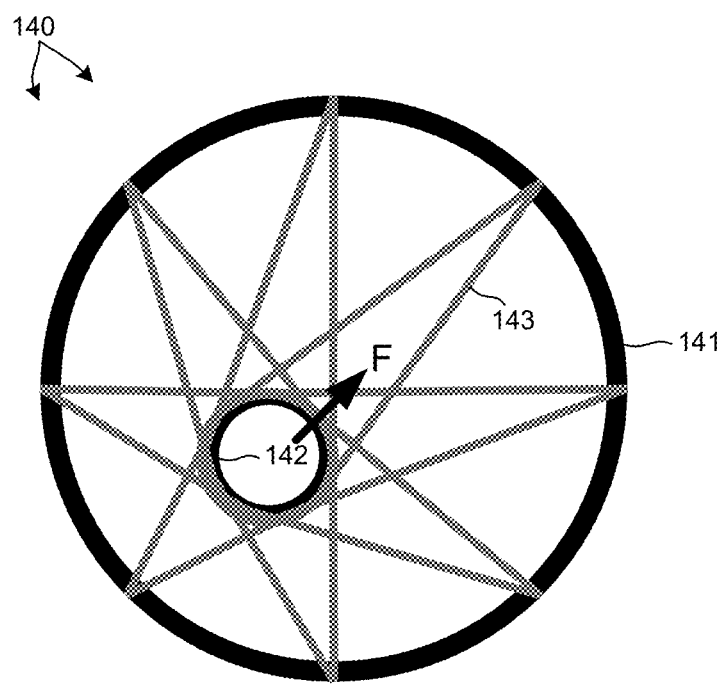
FIG. 9B depicts compliant toroid 140 in a deformed position.

FIGS. 9A-9B depict one embodiment of a compliant toroid 140 in two different operational states. As depicted in FIGS. 9A-9B, compliant toroid 140 includes an outer perimeter structure 141 that is fixed to housing 121 during operation and an inner perimeter structure 142 that is fixed to a portion of the extensible body support limb during operation. Compliant toroid 140 includes elastic elements 143 placed in tension and coupled between the inner and outer perimeter structures in a manner similar to a spoked wheel and hub arrangement. In one example, elastic cords 143 are looped around the inner perimeter structure and are secured to the outer perimeter structure with notches. FIG. 9A depicts compliant toroid 140 in a nominal position (i.e., equilibrium position) where no restoring force is generated. FIG. 9B depicts compliant toroid 140 in a deformed position (i.e., displaced from the equilibrium position). In this position, the elastic elements 143 generate a restoring force, F, from the deformed position toward the nominal position.

Figure 10:
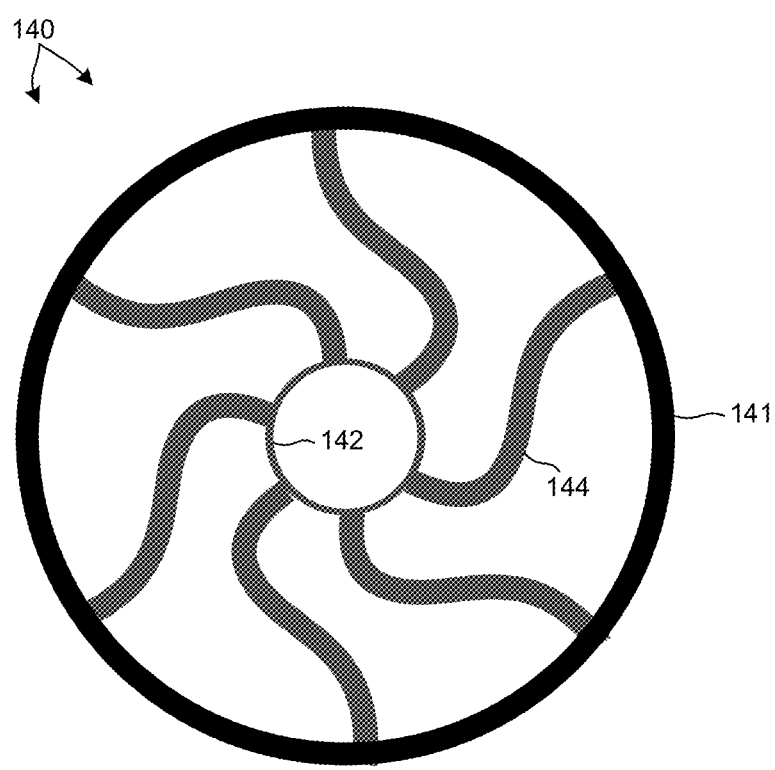
FIG. 10 depicts another embodiment of a complaint toroid 140.

FIG. 10 depicts another embodiment of a complaint toroid 140. As depicted in FIG. 10, compliant toroid 140 includes an outer perimeter structure 141 that is fixed to housing 121 during operation and an inner perimeter structure 142 that is fixed to a portion of the extensible body support limb during operation. Compliant toroid 140 includes flexure elements 144 located between the inner and outer perimeter structures. When compliant toroid 140 is moved to a deformed position (i.e., displaced from the equilibrium position), flexure elements 144 generate a restoring force from the deformed position toward the nominal position. The stiffness of the compliant toroid can be tuned by varying the thickness and the shape of the flexure structures.

In some other embodiments, compliant toroid 140 includes inner and outer perimeter structures and the space in between is filled with an elastomeric material. In general, compliant toroid 140 may include any suitable combination of elastic structures to introduce compliance between the inner and outer perimeter structures.

As depicted in FIG. 8, the effective rotational compliance of the extensible body support limb with respect to housing 121 depends on the distance, D, between compliant toroid 140 and rotational joint 127. As the distance is extended, the joint compliance is reduced (i.e., joint stiffness is increased) for a given compliant toroid. In a further aspect, the distance between the rotational joint and the compliant toroid is adjustable.

Figure 11:
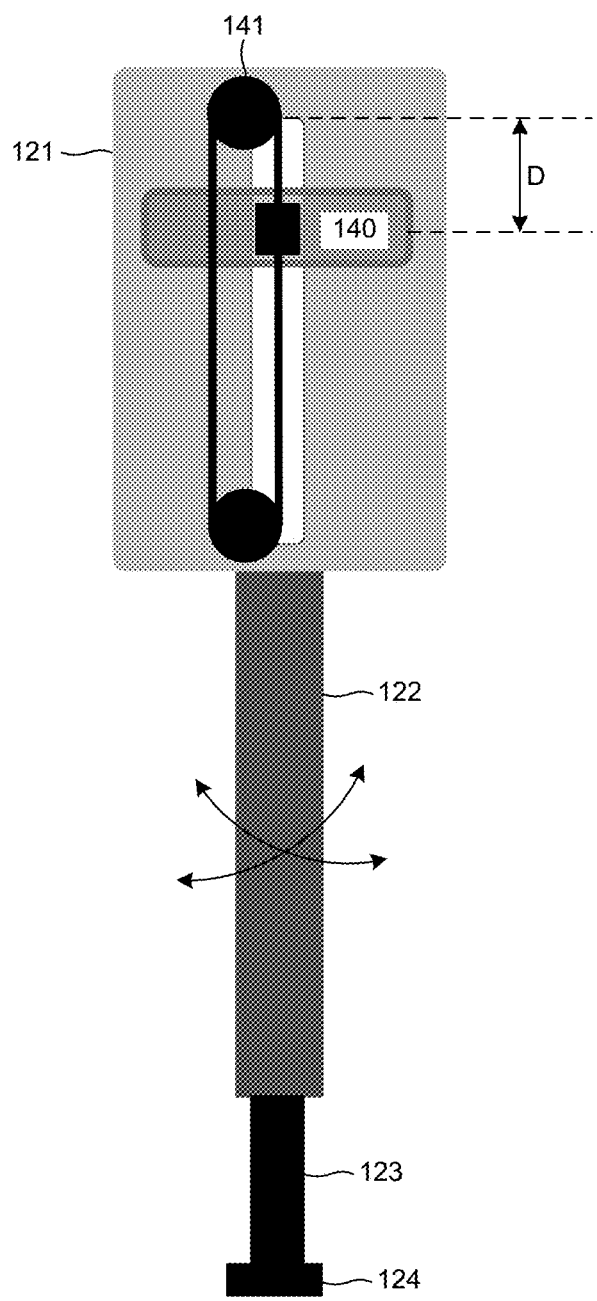
FIG. 11 depicts an illustration of passive upper body support assembly 120 including a belt drive mechanism 141 that adjusts the distance, D, between compliant toroid 140 and rotational joint 127.

FIG. 11 depicts an illustration of passive upper body support assembly 120 including a belt drive mechanism 141 that adjusts the distance, D, between compliant toroid 140 and rotational joint 127. In these embodiments, belt drive mechanism 141 moves compliant toroid 140 with respect to housing 121 and the extensible body support limb to a desired location.

In a further aspect, the distance between compliant toroid 140 and rotational joint 127 is adjustable based on a movement of a control element mounted to the harness assembly within reach of the human user. In one example, the rotation of belt drive mechanism 141 controlled by a rotary cable and sheath arrangement. The rotation of the cable with respect to the sheath is controlled by a control element (e.g., ratcheting dial, lever, etc.) mounted to the harness assembly within reach of the human user. For example, control element 114A controls the position of the belt drive mechanism associated with passive upper body support assembly 120A. Similarly, control element 114B controls the position of the belt drive mechanism associated with passive upper body support assembly 120B. As depicted in FIG. 3, control elements 114A-B are located on the chest of vest 116 and are easily accessible by a hand of the human user.

In general, a passive upper body support assembly may include one or more compliant toroids. Each compliant toroid may have a different compliance and may be located at a different distance from the rotational joint. In addition, each compliant toroid may be selectively decoupled from housing 121, the extensible body support limb, or both. When decoupled, the compliant toroid does not contribute to the joint compliance associated with rotational joint 127. By selectively coupling or decoupling one or more compliant toroids, the effective joint compliance associated with rotational joint 127 is tuned to a desired value. By controlling the distance between two or more compliant toroids and the rotational joint 127 and by also controlling whether or not a one or more of the toroids is coupled between housing 121 and the extensible body support limb, a relatively large range of joint compliance is achievable.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. An upper body support system comprising:
    a harness assembly couplable to a torso of a human user;
    a plurality of passive upper body support assemblies each coupled to the harness assembly, wherein a first of the plurality of passive upper body support assemblies is coupled to the harness assembly on a first side of the torso of the human user, and wherein a second of the plurality of passive upper body support assemblies is coupled to the harness assembly on a second side of the torso of the human user opposite the first side, wherein each of the plurality of passive upper body support assemblies includes:
        a housing coupled to the harness assembly; and
        an extensible body support limb coupled to the housing and extending from the housing toward a surface of a working environment.

2. The upper body support system of claim 1, further comprising:
    a rotational joint that adjustably couples the housing to the harness assembly at a desired orientation of the extensible body support limb with respect to the harness assembly.

3. The upper body support system of claim 2, further comprising:
    a clamping mechanism that fixedly couples the housing to the harness assembly at the rotational joint at the desired orientation.

4. The upper body support system of claim 3, wherein the clamping mechanism is engaged by a movement of a control element mounted to the harness assembly within reach of the human user.

5. The upper body support system of claim 1, wherein the extensible body support limb is coupled to the housing by a rotational joint that allows the extensible body support limb to rotate with respect to the housing in at least one degree of freedom.

6. The upper body support system of claim 5, further comprising:
    a compliant toroid having an outer perimeter coupled to the housing and an inner perimeter coupled to the extensible body support limb, wherein the compliant toroid is located at a distance from the rotational joint.

7. The upper body support system of claim 6, wherein the compliant toroid generates a restoring force in a direction opposite a movement of the extensible body support limb with respect to the housing, wherein the movement of the extensible body support limb with respect to the housing is a rotation of the extensible body support limb with respect to the housing about the rotational joint.

8. The upper body support system of claim 6, wherein the distance from the rotational joint is adjustable.

9. The upper body support system of claim 8, wherein the distance from the rotational joint is adjustable based on a movement of a control element mounted to the harness assembly within reach of the human user.

10. The upper body support system of claim 1, the extensible body support limb comprising:
    a first linear structure coupled to the housing;
    a second linear structure coupled to the first linear structure by a prismatic joint that allows the second linear structure to move with respect to the first linear structure in one linear degree of freedom; and
    a spring element coupled to the first linear structure and the second linear structure that generates a restoring force in a direction opposite a movement of the second linear structure with respect to the first linear structure from a nominal position of the second linear structure with respect to the first linear structure.

11. The upper body support system of claim 10, wherein the nominal position of the second linear structure with respect to the first linear structure is adjustable.

12. The upper body support system of claim 11, wherein the nominal position is adjustable based on a movement of a control element within reach of the human user.

13. The upper body support system of claim 10, the extensible body support limb further comprising:
    a foot element coupled between the second linear structure and the surface of a working environment.

14. An upper body support system comprising:
    a harness assembly couplable to a torso of a human user;
    at least one passive upper body support assembly coupled to the harness assembly comprising:
        a housing coupled to the harness assembly; and
        an extensible body support limb coupled to the housing and extending from the housing toward a surface of a working environment, the extensible body support limb comprising:
            a first linear structure coupled to the housing;
            a second linear structure coupled to the first linear structure by a prismatic joint that allows the second linear structure to move with respect to the first linear structure in one linear degree of freedom; and a spring element coupled to the first linear structure and the second linear structure, wherein the spring element generates a restoring force in a direction opposite a movement of the second linear structure with respect to the first linear structure from a nominal position.

15. The upper body support system of claim 14, further comprising:

a rotational joint that adjustably couples the housing to the harness assembly at a desired orientation of the extensible body support limb with respect to the harness assembly.

16. The upper body support system of claim 14, wherein the extensible body support limb is coupled to the housing by a rotational joint that allows the extensible body support limb to rotate with respect to the housing in at least one degree of freedom.

17. The upper body support system of claim 16, further comprising:

a compliant toroid having an outer perimeter coupled to the housing and an inner perimeter coupled to the extensible body support limb, wherein the compliant toroid is located at a distance from the rotational joint, wherein the compliant toroid generates a restoring force in a direction opposite a movement of the extensible body support limb with respect to the housing, wherein the movement of the extensible body support limb with respect to the housing is a rotation of the extensible body support limb with respect to the housing about the rotational joint.

18. The upper body support system of claim 17, wherein the distance from the rotational joint is adjustable.

19. An upper body support system comprising:

a harness assembly couplable to a torso of a human user;

a first passive upper body support assembly coupled to the harness assembly on a first side of the torso of the human user;

a second passive upper body support assembly coupled to the harness assembly on a second side of the torso of the human user opposite the first side, wherein each of the first and second passive upper body support assemblies is is coupled to the harness assembly by a compliant rotational joint that allows an extensible body support limb to compliantly rotate with respect to the harness assembly in at least one degree of freedom.

20. The upper body support system of claim 19, the extensible body support limb comprising:

a first linear structure coupled to a compliant rotational joint;

a second linear structure coupled to the first linear structure by a prismatic joint that allows the second linear structure to move with respect to the first linear structure in one linear degree of freedom; and a spring element coupled to the first linear structure and the second linear structure that generates a restoring force in a direction opposite a movement of the second linear structure with respect to the first linear structure from a nominal position.

* * * * *